United States Patent [19]

Schiebler et al.

[11] Patent Number: 5,395,828
[45] Date of Patent: Mar. 7, 1995

[54] INOSITOL PHOSPHATE ANALOGUES AS CALCIUM-ANTAGONISTIC SUBSTANCES

[75] Inventors: Werner Schiebler, Flörscheim am Main; Elke Deckert, Frankfurt am Main, both of Germany; Erik Dreef, Leiden, Netherlands; Gijs V. D. Marel, Leiden, Netherlands; Jacques V. Boom, Leiden, Netherlands

[73] Assignee: Hoechst Aktiengesellschaft, Frankfurt am Main, Germany

[21] Appl. No.: 903,485

[22] Filed: Jun. 24, 1992

[30] Foreign Application Priority Data

Jun. 26, 1991 [EP] European Pat. Off. ............ 91110546

[51] Int. Cl.$^6$ ............................................... A61K 31/66
[52] U.S. Cl. ..................................... 514/143; 514/141; 554/74; 558/155; 558/156; 558/161
[58] Field of Search ................. 514/141, 143; 554/79; 558/155, 156, 161; 562/8

[56] References Cited

U.S. PATENT DOCUMENTS 4,515,722  5/1985  Yang et al. ........................ 260/403
5,157,140 10/1992  Siren ................................. 558/155

FOREIGN PATENT DOCUMENTS 0262227  4/1988  European Pat. Off. .
0269105  6/1988  European Pat. Off. .

OTHER PUBLICATIONS

Barry V. L. Potter and Stefan R. Nahorski, "Synthesis and biology of inositol polyphosphate analogues." Biochemical Society Transactions, vol. 20, Jun. 1992.
C. E. Dreef et al., "Synthesis of Racemic 3-Methylphosphonate Analogues of Myo-Inositol 3,4-Bis-and 1,3,4-Trisphosphate," Tetrahedron, vol. 47, No. 26, Mar. 1991, pp. 4709-4722.
Copy of European Search Report dated Sep. 22, 1992.

Primary Examiner—José G. Dees
Assistant Examiner—Deborah D. Carr
Attorney, Agent, or Firm—Finnegan, Henderson, Farabow, Garrett & Dunner

[57]    ABSTRACT

A compound of the formula (I)

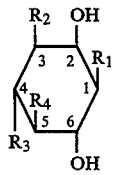

in which
  $R_1$ is e.g. phosphate,
  $R_2$ is e.g. phosphate or OH, and
  $R_4$ is e.g.

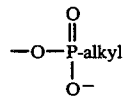

are suitable Calcium antagonists and useful e.g. for the treatment of cardio-vascular diseases.

6 Claims, No Drawings

INOSITOL PHOSPHATE ANALOGUES AS CALCIUM-ANTAGONISTIC SUBSTANCES

BACKGROUND OF THE INVENTION

1. Field of the Invention.

The subject of this invention is a novel group of inositol-phosphat derivatives and their use as calcium-antagonistic compounds for different pharmacological uses such as for the treatment of cardio-vascular diseases.

2. Description of the Prior Art

It is now generally accepted that hydrolysis of phosphatidylinositol(4.5)bisphosphate (PIP2) by receptor- and G-protein mediated activation of PIP2-specific phospholipase C (PIP2-PLC) results in the formation of two different second messengers in the cytoplasm of cells: d-myo inositol(1.4.5)trisphosphate (IP3) and diacylglycerol. IP3 can bind to an appropriate receptor on intracellular organelles causing release of Calcium. Two metabolic pathways terminate this receptor-mediated Calcium release: a) the action of an IP3-3-kinase, phosphorylating the 3-position leading to Inositol (1.3.4.5) tetrakisphosphate (IP4) and b) the action of an IP3-5-phosphatase leading to Inositol(1.4)bisphosphate. Since the cell is expending energy in form of ATP to generate IP4, IP4 is considered to be a putative second messenger, possibly regulating further steps in the Calcium-Metabolism of cells (M. J. Berridge, (1987) Ann. Rev. Biochem. 56, 159-193; and M. J. Berridge and R. F. Irvine, (1989) Nature 341, 197-205). The importance of IP3 as a Calcium mobilizing intracellular second messenger has lead to the synthesis of IP3 and derivatives thereof.

Preparation of Phosphorothioates acting as long-lived agonists have been described (A. M. Cooke et al., (1987) J. Chem. Soc. Chem. Commun. 1525-1526; and J. Strupish et al., (1988) Biochem. J. 253, 901-905). However, there have been no reports in IP3-analogues acting as IP3-receptor- and therefore intracellular Calcium-antagonists. In addition, analogues of IP4 acting as long lived agonists or antagonists, are not available yet.

It is an object of this invention, to describe the synthesis of specific IP3-, IP4- and PIP/PIP2-Analogues modified at the 5-Position. A further surprising aspect of this invention is to describe antagonists of the IP3-receptor, acting as intracellular Calcium-antagonists. These substances Can generally be used as highly active pharmacological compounds, especially they can be used as antithrombotic agents and in a variety of other cardiovascular diseases.

DETAILED DESCRIPTION

Subject of this invention is especially a compound of the formula (I)

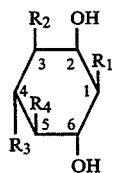

(I)

in which
R1 is 1) phosphate
2) OH
3) 1,2 diacyl-sn-glycer-3-yl phosphate, wherein acyl is a fatty acid with 2 to 20 C-atoms and 0 to 4 C—C-double bonds, or
4) 1,2 dialkyl-sn-glycer-3-yl phosphate, wherein alkyl is a hydrocarbon having 2 to 20 carbon atoms and 0 to 4 C—C-double bonds R2 is
1) OH, or
2) phosphate R3 is
1) phosphate, or
2) OH
3) a radical of formula (II)

wherein
a) $Y=Z=O$ and $X=(C_1-C_8)$-alkyl
b) $Y=Z=O$ and $X=(C_6-C_{18})$-aryl
c) $Y=S$ and $Z=O$ and $X=(C_1-C_8)$-alkyl
d) $Y=S$ and $Z=O$ and $X=(C_6-C_{18})$-aryl
e) $Y=O$ and $Z=X=(C_1-C_8)$-alkyl
f) $Y=O$ and $Z=X=(C_6-C_{18})$-aryl
g) $Y=S$ and $Z=X=(C_1-C_8)$-alkyl
h) $Y=S$ and $Z=X=(C_6-C_{18})$-aryl
i) $Y=Z=O$ and $X=CF_2H$
j) $Y=O$ and $Z=X=F$
k) $Y=Z=O$ and $X=O—(C_1-C_8)$-alkyl
l) $Y=Z=O$ and $X=O—(C_6-C_{18})$-aryl
m) $Y=S$ and $Z=O$ and $X=O—(C_1-C_8)$-alkyl
n) $Y=S$ and $Z=O$ and $X=O—(C_6-C_{18})$-aryl
o) $Y=O$ and $Z=X=O—(C_1-C_8)$-alkyl
p) $Y=O$ and $Z=X=O—(C_6-C_{18})$-aryl
q) $Y=S$ and $Z=X=O—(C_1-C_8)$-alkyl
r) $Y=S$ and $Z=X=O—(C_6-C_{18})$-aryl a radical of formula (III)

where
a) $X=OR$ where R is H, $(C_1-C_8)$-alkyl, or $(C_6-C_{18})$-aryl
b) $X=(C_1-C_8)$-alkyl
c) $X=(C_6-C_{18})$-aryl
d) $X=NH—(C_1-C_8)$-alkyl
e) $X=NH—(C_6-C_{18})$-aryl 5) a radical of formula (IV)

where
a) $X=OR$ where R is H, $(C_1-C_8)$-alkyl or $(C_6-C_{18})$-aryl
b) $X=(C_1-C_8)$-alkyl
c) $X=(C_6-C_{18})$-aryl
d) $X=NH—(C_1-C_8)$-alkyl
e) $X=NH—(C_6-C_{18})$-aryl R4 is 1) a radical of formula (V)

(V)

where
a) Y=Z=O and X=($C_1$-$C_8$)-alkyl
b) Y=Z=O and X=($C_6$-$C_{18}$)-aryl
c) Y=S and Z=O and X=($C_1$-$C_8$)-alkyl
d) Y=S and Z=O and X=($C_6$-$C_{18}$)-aryl
e) Y=O and Z=X=($C_1$-$C_8$)-alkyl
f) Y=O and Z=X=($C_6$-$C_{18}$)-aryl
g) Y=S and Z=X=($C_1$-$C_8$)-alkyl
h) Y=S and Z=X=($C_6$-$C_{18}$)-aryl
i) Y=Z=O and X=$CF_2H$
j) Y=O and Z=X=F
k) Y=Z=O and X=O—($C_1$-$C_8$)-alkyl
l) Y=Z=O and X=O—($C_6$-$C_{18}$)-aryl
m) Y=S and Z=O and X=O—($C_1$-$C_8$)-alkyl
n) Y=S and Z=O and X=O—($C_6$-$C_{18}$)-aryl
o) Y=O and Z=X=O—($C_1$-$C_8$)-alkyl
p) Y=O and Z=X=O—($C_6$-$C_{18}$)-aryl
q) Y=S and Z=X=O—($C_1$-$C_8$)-alkyl
r) Y=S and Z=X=O—($C_6$-$C_{18}$)-aryl 2) a radical of formula (VI)

(VI)

wherein
a) X=OR where R is H, ($C_1$-$C_8$)-alkyl, or ($C_6$-$C_{18}$)-aryl
b) X=($C_1$-$C_8$)-alkyl
c) X=($C_6$-$C_{18}$)-aryl
d) X=NH—($C_1$-$C_8$)-alkyl
e) X=NH—($C_6$-$C_{18}$)-aryl 3) a radical of formula (VII)

(VII)

wherein
a) X=OR where R is H, ($C_1$-$C_8$)-alkyl or ($C_6$-$C_{18}$)-aryl
b) X=($C_1$-$C_8$)-alkyl
c) x=($C_6$-$C_{18}$)-aryl
d) X=NH—($C_1$-$C_8$)-alkyl
e) X=NH—($C_6$-$C_{18}$)-aryl and the physiologically tolerated salts thereof. Preferred are those compounds of the formula (I) in which R1 is phosphate or 1,2-diacyl-sn-glycer-3-yl-phosphate, wherein acyl is a fatty acid radical having 2 to 20 carbon atoms and 0 to 4 C—C-double bonds,
R2 is OH or phosphate,
R3 is OH or phosphate,
R4 is a radical of formula (V),

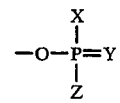
(V)

wherein Y=Z=O and X=($C_1$-$C_8$)-alkyl, and the physiologically tolerated salts thereof.

Furthermore the radical $R^4$ has the following preferred definition:

R4 is a radical of the formula (V) wherein X is methyl, ethyl or propyl.

Another part of the invention is the general synthesis of inositol phosphate derivatives of the formula (I) starting with myo-inositol derivatives like for instance a 3,6-di-O-allyl-1-2-O-cyclohexylidene-myo-inositol (1), proceeding through synthesis of e.g. 3,6-di-O-allyl-4-O-benzyl-1,2-O-cyclohexylidene-myo-inositol (2b) (the respective numbering using the 1-position of the natural Inositol(1.4.5)trisphosphate would be 1,4-di-O-allyl-6-O-benzyl-2,3-O-cyclohexylidene-myo-inositol).

Through a series of protection and deprotection steps which are generally known to a person skilled in this field, using protection of the 5-position with e.g. a —)-p-methoxybenzyl-group, 5-position analogues of both Inositol(1.4.5)trisphosphate and Inositol(1.3.4.5)-tetrakisphosphate can be synthesized.

The compounds of formula (I) can act as calcium-antagonists.

Accordingly, these compounds (inositol phosphate analogues) administered in the appropriate formulation and appropriate dosis, can act as different pharmacological agents, e.g. as antithrombotic agents. Since contraction of smooth muscles also depend on intracellular release of Calcium, vasorelaxant effects of the compounds can be used to treat diseases like hypertension. General calcium-antagonistic effects of the compounds can be exploited to treat diseases like Asthma, Cardiomyopathy, Atherosclerosis, Ischemia (Heart and Brain) and Inflammatory Diseases.

The compounds can be applied in the appropriate dosis, preferably 0.01–100 mg/kg, either orally, intranasally, intraperitoneally, intravenously, topically, or subcutaneously. Dosis and application depends on the species, preferably mammals, bodyweight and age.

Pharmaceutical preparations contain an effective amount of the compound together with a suitable vehicle like e.g. a compatible inorganic or organic carrier. The usual additions for the respective oral, intravenous, topical etc. applications can be used.

The invention is further illustrated by the following examples. In the experimental part the synthesis is outlined by the following schemes A, B and C.

Scheme A
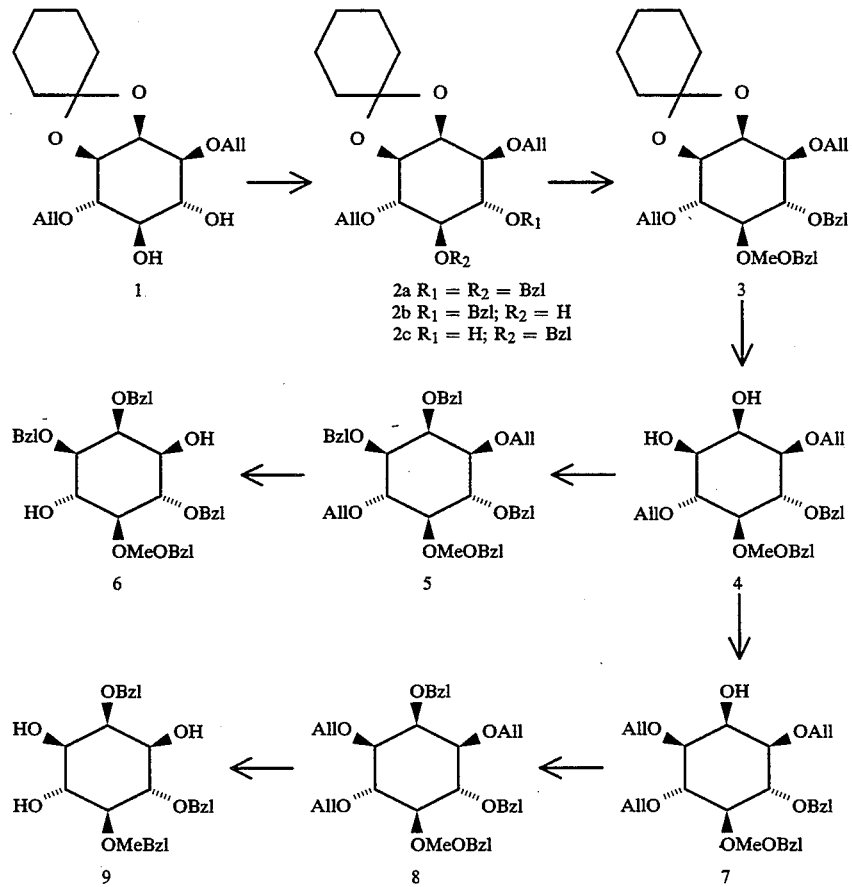
Scheme B
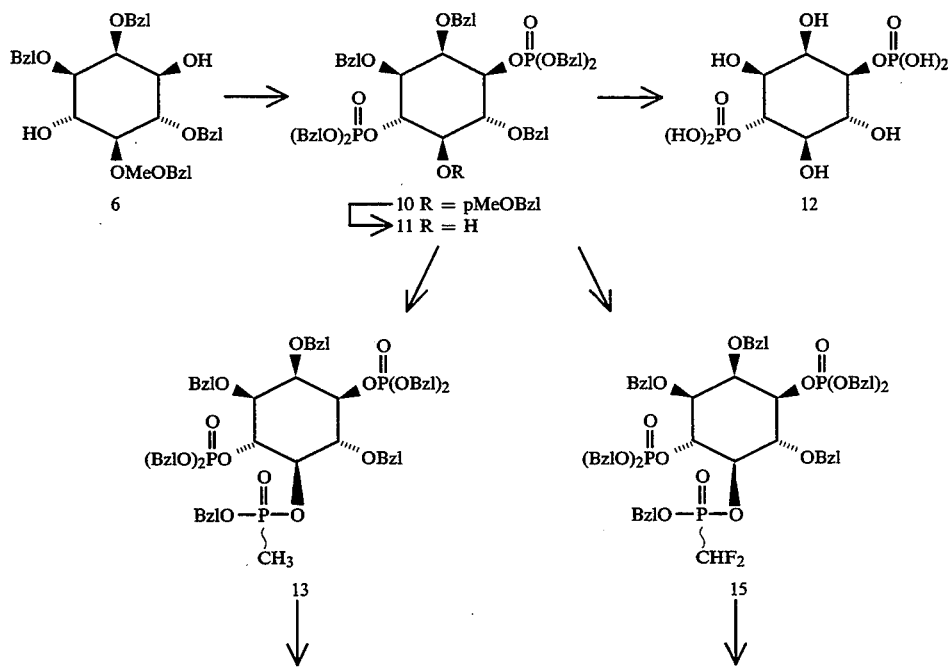

-continued
Scheme B

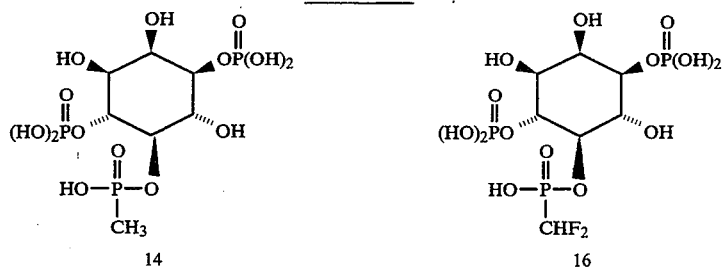

Scheme C

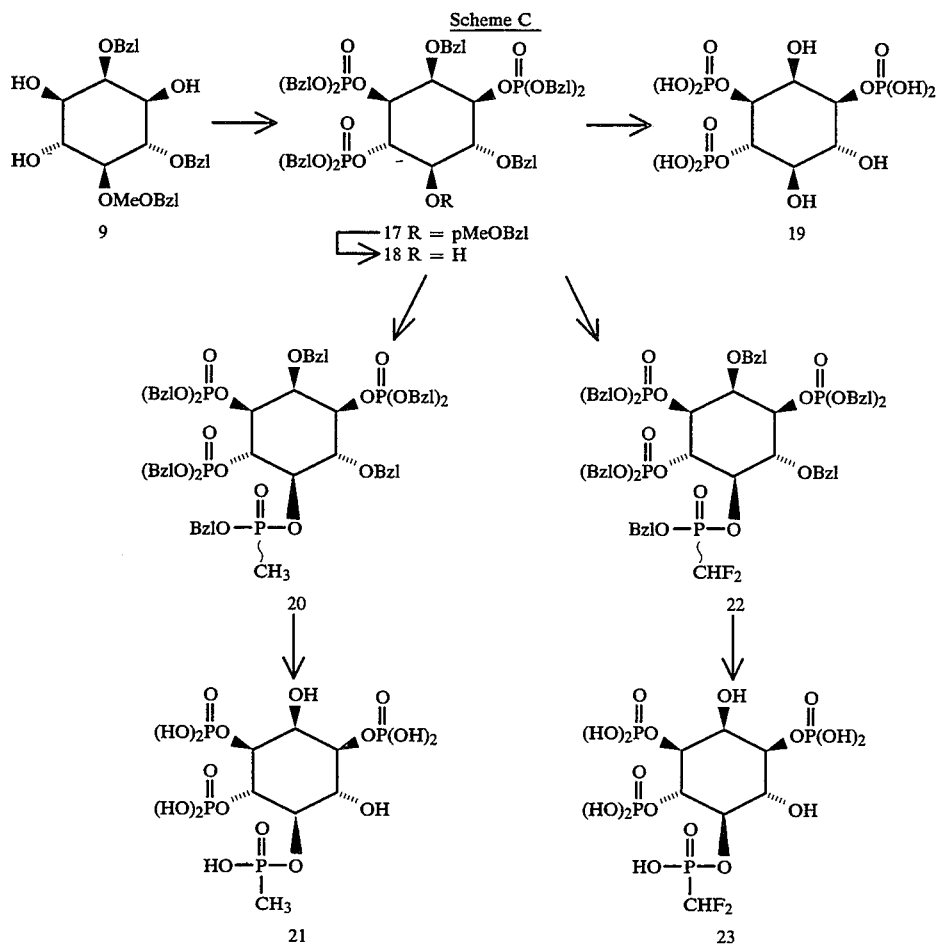

EXAMPLES

Synthesis of myo-inositol 5-methylphosphonate 1,4-bisphosphate

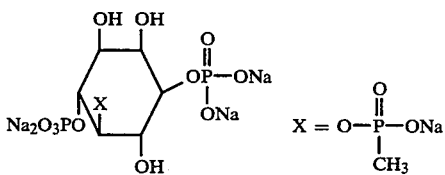

a) 3,6-di-O-allyl-4,5-di-O-benzyl-1,2-O-cyclohexylidene-myo-inositol (2a), 3,6-di-O-allyl-4-O-benzyl-1,2-O-cyclohexylidene-myo-inositol (2b) and 3,6-di-O-allyl-5-O-benzyl-1,2-O-cyclohexylidene-myo-inositol (2c)

To a solution of compound 1, (see C. E. Dreef et al., Recl. Trav. Chim Pays-Bas, 106, 161 (1987)), (6.80 g, 20.00 mmol) and tetrabutylammonium hydrogen sulfate (6.78 g, 20.00 mmol) in $CH_2Cl_2$ (200 mL) were added benzyl bromide (3.00 mL, 25.23 mmol) and 5% aqueous NaOH (200 mL). The reaction mixture was refluxed for 24 h. The organic layer was separated and washed with $H_2O$, 1M $NaHCO_3$ and $H_2O$. The organic layer was dried over $MgSO_4$ and concentrated in vacuo. Silica gel column chromatography (140 g, elution: hexane/$Et_2O$, 100/0 to 50/50, v/v) of the crude product mixture afforded:

Compound 2a (0.52 g, 5% yield) as an oil);

$^1$H-NMR ($CDCl_3$): delta 1.27–1.80 (m, 10H, 5×$CH_2$, cyclohexylidene), 3.37 (dd, 1H, H-5, $J_{5,6}$=9.5 Hz), 3.63 (dd, 1H, H-3, $J_{3,4}$=8.5 Hz), 3.68 (dd, 1H, H-6, $J_{6,1}$=7.0 Hz), 3.87 (dd, 1H, H-4, $J_{4,5}$=8,5 Hz), 4.07 (dd, 1H, H-1, $J_{1,2}=5.5$ Hz), 4.18–4.29 (m, 3H, 2×OCH$_2$, All), 4.34–4.43 (m, 1H, 2×OCH$_2$, All), 4.39 (dd, 1H, H-2, $J_{2,3}=4.0$ Hz), 4.77–4.85 (m, 4H, 2×OCH$_2$, Bzl), 5.14–5.20 (m, 4H, 2×=CH$_2$, All), 5,89–6.05 (m, 2H, 2×—CH=, All), 7.25–7.38 (m, 10H, CH, H aromatic).

Compound 2b (4.56 g, 53% yield) as an oil;

$^1$H-NMR (CDCl$_3$): delta 1.25–1.82 (m, 10H, 5×CH$_2$, cyclohexylidene), 2.69 (d, 1H, 5-OH (exchangeable)) 3.46 (ddd, 1H, H-5, $J_{5,6}=9.5$ Hz, $J_{5,OH}=2.0$ Hz), 3.60 (dd, 1H, H-6, $J_{6,1}=7.0$ Hz), 3.64 (dd, 1H, H-3, $J_{3,4}=8.0$ Hz), 3.76 (dd, 1H, H-4, $J_{4,5}=8.0$ Hz), 4.07 (dd, 1H, H-1, $J_{1,2}=5.5$ Hz), 4.19–4.25 (m, 3H, 2×OCH$_2$, All) 4.37–4.43 (m, 1H, 2×OCH$_2$, All), 4.41 (dd, 1H, H-2, $J_{2,3}=4.0$ Hz), 4.77–4.91 (m, 2H, OCH$_2$, Bzl), 5.17–5.33 (m, 4H, 2×=CH$_2$, All), 5.90–6.01 (m, 2H, 2×—CH=, All), 7.25–7.41 (m, 5H, H aromatic), and compound 2c (3.10 g, 36% yield) as an oil;

$^1$H-NMR (CDCl$_3$): delta 1.26–1.76 (m, 10H, 5×CH$_2$, cyclohexylidene), 2.63, (d, 1H, 4-OH (exchangeable)) 3.25 (dd, 1H, H-5, $J_{5,6}=9.0$ Hz), 3.50 (dd, 1H, H-3, $J_{3,4}=10.0$ Hz), 3.60 (dd, 1H, H-6, $J_{6,1}=7.0$ Hz), 3.97 (ddd, 1H, H-4, $J_{4,5}$ 9.0 Hz, $J_{4,OH}=1.5$ Hz), 4.08 (dd, 1H, H-1, $J_{1,2}=5.0$ Hz), 4.19–4,26 (m, 3H, 2×OCH$_2$, All), 4.33–4.40 (m, 1H, 2H, OCH$_2$, Bzl), 5.15–5.35 (m, 4H, 2×=CH$_2$, All), 5,89–6.02 (m, 2H, 2×—CH=, All), 7.25–7.42 (m, 5H, H aromatic).

b) 1,4-di-O-allyl-6-O-benzyl-5-O-p-methoxybenzyl-myo-inositol (4)

To a solution of compound 2b (4.30 g, 10.00 mmol) and NaH (0.30 g, 12.50 mmol) in dry DMF (50 ml) was added dropwise p-methoxybenzyl chloride (1.50 ml, 11.07 mmol) at 0° C. The reaction mixture was stirred for 2 h at 20° C. Excess NaH was destroyed with MeOH and the reaction mixture concentrated in vacuo. The residue was taken up in CH$_2$Cl$_2$, washed with H$_2$O, 1M NaHCO$_3$ and H$_2$O. The organic layer was dried over MgSO$_4$ and concentrated in vacuo. To a solution of the crude compound 3 in MeOH (25 ml) was added 0.1N HCl in MeOH (25 ml, 2.50 mmol) and the reaction mixture was stirred for 5 h at 20° C. The reaction mixture was neutralized with Et$_3$N and concentrated in vacuo. The residue was taken up in CH$_2$Cl$_2$, washed with H$_2$O, 1M NaHCO$_3$ and H$_2$O. The organic layer was dried over MgSO$_4$ and concentrated in vacuo. Silica gel column chromatography (60 g, solution: CHCL$_2$/MeOH, 100/0 to 95/5, v/v) of the crude product afforded pure 4 (4.09 g, 87% yield), Mp 97°–98° C. (from Et$_2$O/hexane).

$^1$H-NMR (CDCl$_3$): delta 2.52 (s (br), 1H, 2-OH, exchangeable), 2.55 (d, 1H, 3-OH, exchangeable), 3.36 (dd, 1H, H-1, $J_{1,2}=3.0$ Hz), 3.39 (dd, 1H, H-5, $J_{5,6}$ 9.5 Hz), 3.46 (ddd, 1H, H-3, $J_{3,4}=9.5$ Hz, $J_{3,OH}=4.5$ Hz), 3.68 (dd, 1H, H-4, $J_{4,5}=9.5$ Hz), 3.80 (s, 3H, OCH$_3$, pMeOBzl), 3.86 (dd, 1H, H-6, $J_{6,1}=9.5$ Hz), 4.13–4.29 (m, 3H, 2×OCH$_2$, All), 4.22 (dd (br), 1H, H-2, $J_{2,3}=3.0$ Hz, $J_{2,OH}<1.0$ Hz), 4.40–4.47 (m, 1H, 2×OCH$_2$, All), 4.70–4.89 (m, 4H, 2×OCH$_2$, Bzl and pMeOBzl), 5.17–5.34 (m, 4H, 2×=CH$_2$, All) 5.87–6.03 (m, 2H, 2×—CH=, All), 6.82–6.87 and 7.21–7.37 (m, 9H, H aromatic). A separation of the enantiomers may be achieved e.g. by chiral auxiliary groups.

c) 1,4-di-O-allyl-2,3,6-tri-O-benzyl-5-O-p-methoxybenzyl-myo-inositol (5)

To a solution of compound 4 (1.75 g, 3.72 mmol) and NaH (0.23 g, 9.58 mmol) in dry DMF (20 mL) was added dropwise benzyl bromide (1.00 ml, 8.41 mmol) at 0° C. The reaction mixture was stirred for 2 h at 20° C. Excess NaH was destroyed with MeOH and the reaction mixture concentrated in vacuo. The residue was taken up in CH$_2$Cl$_2$, washed with H$_2$O, 1M NaHCO$_3$ and H$_2$O. The organic layer was dried over MgSO$_4$ and concentrated in vacuo. Silica gel column chromatography (30 g, elution: hexane/Et$_2$O, 100/0 to 50/50, v/v) of the crude product yielded 5 (2.30 g, 95% yield, Mp 69.5°–70.5° C. (from pentane).

$^1$H-NMR (CDCl$_3$): delta 3.23 (dd, 1H, H-1, $J_{1,2}=2.5$ Hz), 3.30 (dd, 1H, H-3, $J_{3,4}=10.0$ Hz), 3.38 (dd, 1H, H-5, $J_{5,6}=9.0$ Hz), 3.79 (s, 3H, OCH$_3$, pMeOBzl), 3.91 (dd, 1H, H-4, $J_{4,5}=9.0$ Hz), 3.96 (dd, 1H, H-6, $J_{6,1}=10.0$ Hz), 3.99 (dd, 1H, H-2, $J_{2,3}$ 2.5 Hz), 4.03–4.13 (m, 2H, OCH$_2$, All) 4.29–4.44 (m, 2H, OCH$_2$, All), 4,58–4.90 (m, 8H, 4×OCH$_2$, Bzl and pMeOBzl), 5.13–5.32 (m, 4H, 2×=CH$_2$, All), 5.83–6.06 (m, 2H, 2×—CH=, All), 6.82–6.86 and 7.22–7.41 (m, 19H, H aromatic).

d) 2,3,6-tri-O-benzyl-5-O-p-methoxybenzyl-myo-inositol (6)

To a solution of compound 5 (1.95 g, 3.00 mmol) in 1,2-dichloroethane (15 ml) under an inert helium atmosphere was added 1,5-cyclooctadiene-bis[methyldiphenylphosphine]iridium hexafluorophosphate (see L. M. Haines et al., J. Chem. Soc. Dalton Trans., 1891 (1972)), (20 mg) in 1,2-dichloroethane (0.5 ml). The catalyst was activated by passing over a stream of hydrogen for 2 min. The solution was degassed and left under a stream of argon for 4 h. The reaction mixture was concentrated in vacuo and the crude 2,3,6-tri-O-benzyl-5-O-p-methoxybenzyl-1,4-di-O-trans-prop-1-enyl-myo-inositol, thus obtained was used without further purification.

To a solution of the crude 2,3,6-tri-O-benzyl-5-O-p-methoxybenzyl-1,4-di-O-trans-prop-1-enyl-myop-inositol in CH$_2$Cl$_2$ (15 ml) was added 0.2N HCl in MeOH (15 ml, 3.00 mmol) and the reaction mixture was stirred for 1 h at 20° C. The reaction mixture was neutralized with Et$_3$N and concentrated in vacuo. The residue was taken up in CH$_2$Cl$_2$, washed with H$_2$O, 1M NaHCO$_3$ and H$_2$O. The organic layer was dried over MgSO$_4$ and concentrated in vacuo. Silica gel column chromatography (25 g, elution: CH$_2$Cl$_2$/acetone, 100/0 to 97/3, v/v) of the crude product afforded pure 6 (1.58 g, 92% yield). Mp 97.5°–98.5° C. (from Et$_2$O/hexane).

$^1$H-NMR (CDCl$_3$): delta 2.28 (d, 1H, 1-OH, exchangeable), 2.52 (d, 1H, 4-OH, exachangeable), 3.30 (dd, 1H, H-3, $J_{3,4}=10.0$ Hz), 3.38 (dd, 1H, H-5, $J_{5,6}=9.0$ Hz), 3.52 (ddd, 1H, H-1, $J_{1,2}=2.5$ Hz; $J_{1,OH}=6.5$ Hz), 3.78 (dd, 1H, H-6, $J_{6,1}=9.5$ Hz), 3.80 (s, 3H, OCH$_3$, pMeOBzl), 4.07 (dd, 1H, H-2, $J_{2,3}=2.5$ Hz), 4.14 (ddd, 1H, H-4, $J_{4,5}=9.0$ Hz, $J_{4,OH}=1.5$ Hz), 4.59–4.94 (m, 8H, 4×OCH$_2$, Bzl and pMeOBzl), 6.84–6,89 and 7.21–7.40 (m, 19H, H aromatic).

e) 2,3,6-tri-O-benzyl-5-O-p-methoxybenzyl-myo-inositol 1,4-bis-(dibenzylphosphate) (10)

A mixture of compound 6 (1.43 g, 2.51 mmol) and N,N-diisopropyldibenzyl phosphoramidite (see K.-L. Yu and B. Fraser-Reid, Tetrahedron Lett., 29, 979 (1988)) (2.60 g, 7.54 mmol) was coevaporated with toluene (2×25 ml) and dissolved in CH$_2$Cl$_2$ (20 ml). Subsequently a solution of 1H-tetrazole (0.65 g, 9.29 mmol) in CH$_3$CN (20 ml) was added and the reaction mixture was stirred for 15 min. $^{31}$P-NMR showed the presence of two peaks (delta 141.04 and 141.88). The reaction mixture was cooled (0° C.) and tert.-butyl hydroperoxide (3.75 ml) was added and stirring was continued for 45 min at 0° C. The reaction mixture was diluted with CH$_2$Cl$_2$ and washed with H$_2$O. The organic layer was dried over MgSO$_4$ and concentrated in vacuo. Silica gel column chromatography (35 g, elution: hexane/EtOAc, 100/0 to 25/75, v/v) of the crude product afforded homogeneous 10 (2.57 g, 94% yield) as an oil.

$^{31}$P-NMR (CH$_2$Cl$_2$): delta −1.03 (2 P)

f) 2,3,6-tri-O-benzyl-myo-inositol 1,4-bis(dibenzylphosphate) (11)

To a solution of compound 10 (2.18 g, 2.00 mmol) in CH$_2$Cl$_2$ (48.75 ml) was added trifluoroacetic acid (1.25 ml) and the reaction mixture was stirred for 30 min at 20° C. The reaction mixture was diluted with CH$_2$Cl$_2$ and washed with H$_2$O, 1M Tetraethylammonium bicarbonate buffer (TEAB) and H$_2$O. The organic layer was dried over MgSO$_4$ and concentrated in vacuo. Silica gel column chromatography (25 g, elution: hexane/EtOAc, 100/0 to 25/75, v/v) of the crude product afforded pure 11 (1.59 g, 82% yield), as an oil.

$^{31}$P-NMR (CH$_2$Cl$_2$): delta −1.24 (1 P) and 0.76 (1 P).

g) 2,3,6-tri-O-benzyl-myo-inositol 5-(benzyl methylphosphonate) 1,4-bis(dibenzylphosphate) (13)

A solution of bis(1-[6-trifluoromethyl]benzotriazolyl) methylphosphonate in dioxane (0.2M, 3.5 ml, 0.70 mmol) was added to compound 11 (0.34 g, 0.35 mmol), which had been dried by repeated coevaporation with pyridine. The reaction was stirred for 30 min at 20° C. Subsequently benzyl alcohol (0.15 ml, 1.45 mmol) and N-methylimidazole (0.15 ml, 1.88 mmol) were added and the reaction mixture was stirred for another 1 h at 20° C. After addition of 1M TEAB the reaction mixture was diluted with CH$_2$Cl$_2$ and washed with H$_2$O, 1M TEAB and H$_2$O. The organic layer was dried over MgSO$_4$ and concentrated in vacuo. Silica gel column chromatography (5 g, elution: hexane/EtOAc, 100/0 to 25/75, v/v) of the crude product afforded pure 13 (0.30 g, 75% yield), as an oil.

$^{31}$P-NMR (CH$_2$Cl$_2$): delta −1.27 (2 P); 31.31 and 32.88 (1P, ratio, 1/3).

h) myo-inositol 5-methylphosphonate 1,4-bisphosphate (Na+-form) (14)

Compound 13 (225 mg, 0.20 mmol) was dissolved in a mixture of MeOH and H$_2$O (50 ml, 4/1, v/v) and hydrogenated over 10% palladium on charcoal (0.20 g) at 500 kPa for 16 h at 20° C. The solution was filtered and concentrated in vacuo (30° C.) to a small volume. After Sephadex C-25 (Na+-form, 4.5 g, 10.4 mmol) cation-exchange and lyophilization 14 (101 mg, 97% yield) was obtained, as a white solid.

$^{31}$P-NMR (D$_2$O, pH=2.00): delta 0.29 (P-1), 1.20 (P-4) and 31.68 (P-5). $^1$H-NMR (D$_2$O, pH=2.00): delta 1.48 (d, 3H, CH$_3$, J$_{H,P}$32 17.5 Hz), 3.75 (dd, 1H, H-3, J$_{3,4}$=10.0 Hz), 3.88 (dd, 1H, H-6, $_{6,1}$=10.0 Hz), 4.03 (ddd, 1H, H-1, J$_{1,2}$=2.5 Hz, J$_{H,P}$=8.5 Hz), 4.12 (ddd, 1H, H-5, J$_{5,6}$=9.5 Hz, J$_{H,P}$=9.0 Hz), 4.28 (dd, 1H, H-2, J$_{2,3}$=3.0 Hz), 4.34 (ddd, 1H, H-4, J$_{4,5}$=9.0 Hz, J$_{H,P}$=9.0 Hz).

Example 1b

Pharmacological activity of the compound of example 1

The activity of myo-inositol 5-methylphosphonate 1.4-bisphosphate (IP2-5-MP) as a Calcium antagonist in human platelets is shown as follows.

Human platelets were purified in the presence of citrate by differential centrifugation and resuspended to ca 1×10exp9 cells/ml in Tyrode-HEPES-(N-2-hydroxyethyl-piperazine-N′-2 ethane-sulfonic acid)-buffer pH 7.4 containing 0.2% w/v Bovine Serum Albumin and 1 mM EGTA (Ethylene Glycol Bis (β-Aminoethyl Ether)N,N,N′,N′-Tetraacidic acid). After 20 min, the platelets were centrifuged again (700×g, 20 min) and resuspended to the same concentration in 4 ml of "assay-buffer" containing:

110 mM Potassiumchloride
1.2 mM Potassiumdihydrogenphosphate
5 mM Potassiumsuccinate
5 mM Potassiumpyruvate
5 mM Potassium-ATP
6.8 mM Magnesiumchloride
9.8 U/ml Creatine kinase
12 mM Creatine phosphate
25 mM HEPES-buffer, pH as indicated After a further 30 min, the platelet suspension was diluted 5-fold into assay-buffer containing 2 μM Quin2 (2-[[2-[bis(carboxymethyl)amino]-5-methyl-phenoxy]-methyl]-6-methoxy-8-[bis(β-aminoethyl)amino]quinoline) salt as a fluorescence indicator for Calcium. To this suspension Saponin was added to a final concentration of 20 μg/ml to permeabilize the cells. The fluorescence of the suspension was continually monitored with a fluorescence spectrometer until a stable baseline was achieved. At this point, IP3 was added and the resulting release of Calcium measured as an increase in the intensity of the Quin2-fluorescence. An EC$_{50}$ (effective concentration) value of 2×10exp−7M was obtained at pH 7.4. IP2-5-MP itself had no effect on release of Calcium. However, when applied at 10exp−4M 15 sec before addition of 5×10exp−7M IP3, at pH values below 7.4 the Calcium response to IP3 was inhibited.

The following Inhibiton-values were found at the indicated concentrations of IP3 (5×10−7M) and IP2-5-MP (1×10−4M):

| pH | Inhibition of Calcium release (%) |
|---|---|
| 7.6 | 0 |
| 7.4 | 0 |
| 7.3 | 68 |
| 7.2 | 100 |
| 7.1 | 100 |

Example 2

Synthesis of myo-inositol 5-ethylphosphonate 1,4-bisphosphate (Na+-form)

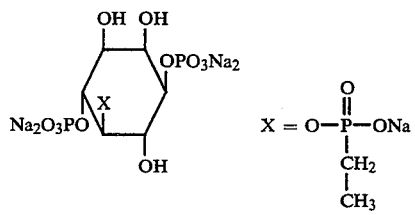

To compound 11 a solution of bis(1-[6-trifluormethyl]ethyl)phosphonate was added under identical conditions as for compound 13. Following the amounts and reaction conditions as given for the compounds 13–14, the final product myo-inositol 5-ethylphosphonate 1,4-bisphosphate (Na+-form) was synthesized.

$^{31}$P-NMR-Signals: (D$_2$O): delta−3.54 (P-1 and P-4), 32,70 (P-5).

Example 3

Synthesis of myo-inositol 5-((difluoromethyl)phosphonate) 1,4-bis-phosphate (Na+-form)

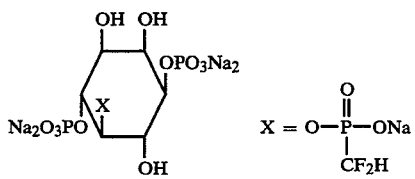

a) 2,3,6-tri-O-benzyl-myo-inositol 5-(benzyl(difluoromethyl)phosphonate) 1,4-bis(dibenzylphosphate) (15)

A solution of (difluoromethyl)phosphonic di(1,2,4-triazolide) in dioxane (0.2M, 3.5. ml, 0.780 mmol) was added to compound 11 (0.34 g, 0.35 mmol), which had been dried by repeated coevaporation with pyridine. The reaction was stirred for 30 min at 20° C. Subsequently benzyl alcohol (0.15 ml, 1.45 mmol) and N-methylimidazole (0.15 ml, 1.88 mmol) were added and the reaction mixture was stirred for another 1 h at 20° C. After addition of 1M TEAB the reaction mixture was diluted with $CH_2Cl_2$ and washed with $H_2O$, 1M TEAB and $H_2O$. The organic layer was dried over $MgSO_4$ and concentrated in vacuo. Silica gel column chromatography (5 g, elution: Hexane/EtOAc, 100/0 to 25/75, v/v) of the crude product afforded pure 15 (0.29 g, 70% yield), as an oil.

$^{31}$P-NMR ($CH_2Cl_2$: delta −1.45, −1.36, −1.18 and −1.00 (2 P); 4.32 ($J_{P,F}$=93.0 Hz) and 6.66 ($J_{P,F}$=85.5 Hz and $J_{P,F}$F=97.5 Hz) (1 P).

b) myo-inositol 5-((difluoromethyl)phosphonate) 1,4-bisphosphate (Na+-form) (16)

Compound 15 (220 mg, 0.19 mmol) was dissolved in a mixture of MeOH and $H_2O$ (50 ml, 4/1, v/v) and hydrogenated over 10% palladium on charcoal (0.20 g) at 500 kPa for 16 h at 20° C. The solution was filtered and concentrated in vacuo (30° C.) to a small volume. After Sephadex C-25 (Na+-form, 4.0 g, 9.2 mmol) cation-exchange and lyophilization 16 (0.10 g, 95% yield) was obtained, as a white solid.

$^{31}$P-NMR ($D_2O$, pH=2.00): delta 0.27 (P-1), 1.16 (P-4) and 4.68 (P-5, JP, F=85.0 Hz).

Example 4

Synthesis of myo-inositol 5-methylphosphonate 1,3,4-trisphosphate (Na+-form)

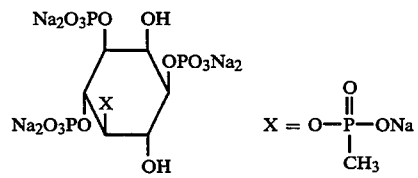

a) 1,3,4-tri-O-allyl-6-O-benzyl-5-O-p-methoxybenzyl-myo-inositol (7)

A solution of compound 4 (2.00 g, 4.26 mmol) and dibutyltin oxide (1.20 g, 4.82 retool) in dry MeOH (25 ml) was refluxed for 2.5 h and subsequently concentrated in vacuo. The residue was coevaporated with toluene (3×25 ml), dissolved in dry DMF (45 ml) and subsequently cesium fluoride (0.85 g, 5.59 mmol) and allyl bromide (0.55 mL, 6.50 mmol) were added. After stirring for 16 h at 20° C. the reaction mixture was concentrated in vacuo. The residue was taken up in $Et_2O$, washed with $H_2O$, 1M $NaHCO_3$ and $H_2O$. The organic layer was dried over $MgSO_4$ and concentrated in vacuo. Silica gel column chromatography (30 g, elution: hexane/EtOAc, 100/0 to 50/50, v/v) of the crude product afforded pure 7 (1.81 g, 83% yield). Mp 77°–78° C. (from $Et_2O$/pentane).

$^1$H-NMR ($CDCl_3$): delta 2.42 (s (br), 1H, 2-OH, exchangeable), 3.25 (dd, 1H, H-3, $J_{3,4}$=9.5 Hz), 3.29 (dd, 1H, H-1, $J_{1,2}$=3.0 Hz), 3.36 (dd, 1H, H-5, $J_{5,6}$=9.5 Hz), 3.77 (dd, 1H, H-4, $J_{4,5}$=9.5 Hz), 3.80 (s, 3H, $OCH_3$, pMeOBzl), 3.87 (dd, 1H, H-6, $J_{6,1}$=9.5 Hz), 4.18–4.22 (m, 4H, 2×$OCH_2$, All), 4.21 (rid (br), 1H, H-2, $J_{2,3}$=3.0 Hz), 4.25–4.39 (m, 2H, OCH=, All), 4.72–4.87 (m, 4H, 2×$OCH_2$, Bzl and pMeOBzl), 5.14–5.35 (m, 6H, 3×=$CH_2$, All), 5.88–6.05 (m, 3H, 3×—CH=, All), 6.82–6.87 and 7.23–7.38 (m, 9H, H aromatic).

b) 1,3,4-tri-O-allyl-2,6-di-O-benzyl-5-O-p-methoxybenzyl-myo-inositol (8)

To a solution of compound 7 (1.75 g, 3.43 mmol) and NaH (0.11 g, 4.58 mmol) in dry DMF (20 ml) was added dropwise benzyl bromide (0.45 ml, 3.78 mmol) at 0° C. The reaction mixture was stirred for 2 h at 20° C. Excess NaH was destroyed with MeOH and the reaction mixture concentrated in vacuo. The residue was taken up in $CH_2Cl_2$, washed with $H_2O$, 1M $NaHCO_3$ and $H_2O$. The organic layer was dried over $MgSO_4$ and concentrated in vacuo. Silica gel column chromatography (30 g, elution: hexane/$Et_2O$, 100/0 to 50/50, v/v) of the crude product yielded 8 (1.96 g, 95% yield) as an oil. Mp 39.5°–40.5° C. (solidified).

$^1$H-NMR ($CDCl_3$): delta 3.19 (dd, 1H, H-3, $J_{3,4}$=10.0 Hz), 3.24 (dd, 1H, H-1, $J_{1,2}$=2.5 Hz), 3.37 (dd, 1H, H-5, $J_{5,6}$=9.0 Hz), 3.79 (s, 3H, $OCH_3$, pMeOBzl), 3.86 (dd, 1H, H-4, $J_{4,5}$=9.0 Hz), 3.96 (dd, 1H, H-6, $J_{6,1}$=10.0 Hz), 3.99 (dd, 1H, H-2, $J_{2,3}$=2.5 Hz), 4.02–4.16 (m, 4H, 2×$OCH_2$, All), 4.26–4.41 (m, 2H, $OCH_2$, All), 4.69–4.90 (m, 6H, 3×$OCH_2$, Bzl and pMeOBzl), 5.13–5.34 (m, 6H, 3×=$CH_2$, All), 5.85–6.06 (m, 3H, 3×—CH=, All), 6.82–6.86 and 7.23–7.44 (m, 14H, H aromatic).

c) 2,6-di-O-benzyl-5-O-p-methoxybenzyl-myo-inositol (9)

To a solution of compound 8 (1.80 g, 3.00 mmol) in 1,2-dichloro-ethane (15 ml) under an inert helium atmosphere was added 1,5-cyclooctadiene-bis[methyldiphenylphosphine]iridium hexafluoro-phosphate (see L. M. Haines et al., J. Chem. Soc. Dalton Tans. 1891 (1972)) (20 mg) in 1,2-dichloroethane (0.5 ml). The catalyst was activated by passing over a stream of hydrogen for 2 min. The solution was degassed and left under a stream of argon for 4 h. The reaction mixture was concentrated in vacuo and the crude 2,6-di-O-benzyl-5-O-p-methoxybenzyl-1,3,4-tri-O-trans-prop-1-enyl-myo-inositol, thus obtained was used without further purification.

To a solution of the crude 2,6-di-O-benzyl-5-O-p-methoxybenzyl-1,3,4-tri-O-trans-prop-1-enyl-myo-inositol in $CH_2Cl_2$ (15 ml) was added 0.2N HCl in MeOH (15 ml, 3.00 mmol) and the reaction mixture was stirred for 1 h at 20° C. The reaction mixture was neutralized with $Et_3N$ and concentrated in vacuo. The residue was taken up in $CH_2Cl_2$, washed with $H_2O$, 1M $NaHCO_3$ and $H_2O$.

The organic layer was dried over $MgSO_4$ and concentrated in vacuo. Silica gel column chromatography (20 g, elution: CH2Cl2/MeOH, 100/0 to 95/5, v/v) of the crude product afforded pure 9 (1.31 g, 91 yield). Mp 108.5°–109.5° C. (from CH2Cl2/hexane).

1H-NMR (CDCl3): delta 2.33 (d, 1H, 1-OH, exchangeable), 2.38 (d, 1H, 3-OH, exchangeable), 2.48 (d, 1H, 4-OH, exchangeable), 3.32 (dd, 1H, H-5, J5,6=9.0 Hz), 3.46 (ddd, 1H, H-3, J3,OH=9.5 Hz, J3,OH=7.0 Hz), 3.57 (ddd, 1H, H-1, J1,2=2.5 Hz, J1,OH=5.0 Hz), 3.77 (dd, 1H, H-6, J6,1=9.5 Hz), 3.80 (s, 3H, OCH3, pMeOBzl), 3.82 (ddd, 1H, H-4, J4,5=9.0 Hz, J4,OH=2.0 Hz), 4.01 (dd, 1H, H-2, J2,3=2.5 Hz), 4.71–4.95 (m, 6H, 3×OCH2, Bzl and pMeOBzl), 6.85–6.89 and 7.25–7.39 (m, 14H, H aromatic).

d) 2,6-di-O-benzyl-5-O-p-methoxybenzyl-myo-inositol 1,3,4-tris(dibenzylphosphate) (17)

A mixture of compound 9 (1.20 g, 2.50 mmol) and N,N-diisopropyl dibenzyl phosphoramidite (see K.-L. Yu and B. Fraser-Reid, Tetrahedron Lett. 29, 979 (1988)) (3.90 g, 11.30 mmol) was coevaporated with toluene (2×25 ml) and dissolved in CH2Cl2 (30 ml). Subsequently a solution of 1H-tetrazole (1.00 g, 14.29 mmol) in CH3CN (30 mL) was added and the reaction mixture was stirred for 15 min. 31P-NMR showed the presence of three peaks (delta 141.10, 141.19 and 142.55). The reaction mixture was cooled (0° C.) and tert-butyl hydroperoxide (5.65 ml) was added and stirring was continued for 45 min at 0° C. The reaction mixture was diluted with CH2Cl2 and washed with H2O, 1M TEAB and H2O. The organic layer was dried over MgSO4 and concentrated in vacuo. Silica gel column chromatography (40 g, elution: hexane/EtOAc, 100/0 to 25/75, v/v) of the crude product afforded homogeneous 17 (2.74 g, 87% yield) as an oil.

31P-NMR (CH2Cl2): delta −1.45 (1 P), −1.12 (1 P) and −0.82 (1 P).

e) 2,6-di-O-benzyl-myo-inositol 1,3,4-tris(dibenzylphosphate) (18)

To a solution of compound 17 (2.52 g, 2.00 mmol) in CH2Cl2 (48.75 ml) was added trifluoroacetic acid (1.25 ml) and the reaction mixture was stirred for 30 min at 20° C. The reaction mixture was diluted with CH2Cl2 and washed with H2O, 1M TEAB and H2O. The organic layer was dried over MgSO4 and concentrated in vacuo. Silica gel column chromatography (30 g, elution: hexane/EtOAc, 100/0 to 25/75, v/v) of the crude product afforded pure 18 (1.78 g, 78% yield), as an oil.

31P-NMR (CH2Cl2): delta −1.30 (2 P) and 0.82 (1 P).

f) 2,6-di-O-benzyl-myo-inositol 5-(benzyl methylphosphonate) 1,3,4-tris(dibenzylphosphate) (20)

A solution of bis(1-[6-trifluoromethyl]benzotriazolyl) methyl-phosphonate in dioxane (0.2M, 3.5 ml, 0.70 mmol) was added to compound 18 (0.40 g, 0.35 mmol), which had been dried by repeated coevaporation with pyridine. The reaction was stirred for 30 min at 20° C. Subsequently benzyl alcohol (0.15 ml, 1.45 mmol) and N-methylimidazole (0.15 mL, 1.88 mmol) were added and the reaction mixture was stirred for another 1 h at 20° C. After addition of 1M TEAB the reaction mixture was diluted with CH2Cl2 and washed with H2O, 1M TEAB and H2O. The organic layer was dried over MgSO4 and concentrated in vacuo. Silica gel column chromatography (7.5 g, elution: hexane/EtOAc, 100/0 to 25/75, v/v) of the crude product afforded pure 20 (0.29 g, 63% yield), as an oil.

31P-NMR (CH2Cl2): delta −1.45 (1 P), −1.21 (1 P) and −0.70 (1 P); 31.46 and 33.12 (1 P, ratio, 1/3).

g) myo-inositol 5-methylphosphonate 1,3,4-trisphosphate (Na+-form) (21)

Compound 20 (215 mg, 0.16 mmol) was dissolved in a mixture of MeOH and H2O (50 ml, 4/1, v/v) and hydrogenated over 10% palladium on charcoal (0.20 g) at 500 kPa for 16 h at 20° C. The solution was filtered and concentrated in vacuo (30° C.) to a small volume. After cation-exchange and lyophilization the compound 21 (102 mg, 95% yield) was obtained, as a white solid.

31P-NMR (D2O, pH=2.00): delta 0.25 (P-1), 0.43 (P-3), 0.25 (P-4) and 31.76 (P-5). 1H-NMR (D2O, pH=2.00): delta 1.48 (d, 3H, CH3, JH,P=1.75 Hz), 3.90 (dd, 1H, H-6, J6,1=10.0 Hz), 4.08 (ddd, 1H, H-1, J1,2=2.5 Hz, JH,P=8.5 Hz), 4.18 (ddd, 1H, H-5, J5,6=9.5 Hz, JH,P=9.0 Hz), 4.20 (ddd, 1H, H-3, J3,4=9.5 Hz, JH,P=9.5 Hz), 4.44 (dd, 1H, H-2, J2,3=2.5 Hz), 4.50 (ddd, 1H, H-4, J4,5=9.5 Hz, JH,P=9.5 Hz).

Example 5

Synthesis of myo-inositol 5-ethylphosphonate 1,3,4-trisphosphate (Na+-form)

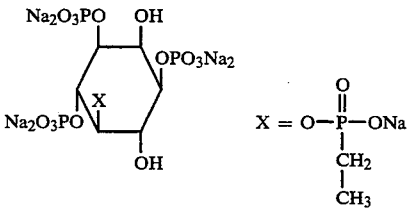

To compound 18 a solution of bis(1-[6-trifluoromethyl]benzotriazolyl)ethylphosphonate was added under identical conditions as for compound 20. Following the amounts and reaction conditions as given for the compounds 20 and 21 the final product, myo-inositol 5-ethylphosphonate 1,3,4-trisphosphate (Na+-form) was synthesized.

FAB-Mass-Spectrometer: Molpeak 666.

Example 6

Synthesis of myo-inositol 5-((difluoromethyl)phosphonate) 1,3,4.trisphosphate (Na+-form)

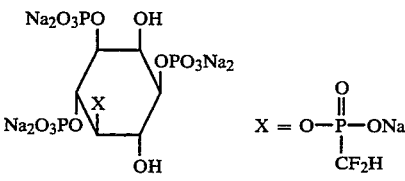

a) 2,6-di-O-benzyl-myo-inositol 5-(benzyl (difluoromethyl)phosphonate) 1,3,4-tris(dibenzylphosphate) (22)

A solution of (difluoromethyl)phosphonic di(1,2,4-triazolide) in dioxane (0.2M, 3.5 ml, 0.70 mmol) was added to compound 18 (0.40 g, 0.35 mmol), which had been dried by repeated coevaporation with pyridine. The reaction was stirred for 30 min at 20° C. Subsequently benzyl alcohol (0.15 ml, 1.45 mmol) and N-methylimidazole (0.15 ml, 1.88 mmol) were added and the reaction mixture was stirred for another 1 h at 20° C. After addition of 1M TEAB the reaction mixture was diluted with CH2Cl2 and washed with H2O, 1M TEAB and H2O. The organic layer was dried over MgSO4 and concentrated in vacuo. Silica gel column chromatography (7.5 g, elution: hexane/EtOAc, 100/0 to 25/75, v/v) of the crude product afforded pure 22 (0.29 g, 61% yield), as an oil.

31P-NMR (CH2Cl2: delta −1.39, −1.15, −0.97 and 0.79 (3 P); 4.35 ($J_{P,F}$=95 Hz) and 6.86 $J_{P,F}$=88.0 Hz and $J_{P,F}$=102.5 Hz) (1 P).

b) myo-inositol 5-((difluoromethyl)phosphonate) 1,3,4-trisphosphate (Na+-form) (23)

Compound 22 (240 mg, 0.18 mmol) was dissolved in a mixture of MeOH and H2O (50 ml, 4/1, v/v) and hydrogenated over 10% palladium on charcoal (0.20 g) at 500 kPa for 16 h at 20° C. The solution was filtered and concentrated in vacuo (30° C.) to a small volume. After cation-exchange and lyophilization compound 23 (114 mg, 93% yield) was obtained, as a white solid.

31P-NMR (D2O, pH=2.00): delta 0.21 (P-1), 0.62 (P-3), 0.62 (P-4) and 4.81 (P-5. $J_{P,F}$=85.5 Hz). 1H-NMR (D2O, pH=2.00): delta 3.91 (dd, 1H, H-6, $J_{6,1}$=10.0 Hz), 4.07 (ddd, 1H, H-1, $J_{1,2}$=2.5 Hz, $J_{H,P}$=8.5 Hz), 4.20 (ddd, 1H, H-5, $J_{5,6}$=9.5 Hz, $J_{H,P}$=9.0 Hz), 4.22 (ddd, 1H, H-3, $J_{3,4}$=9.5 Hz, $J_{H,P}$=9.5 Hz), 4.42 (dd, 1H, H-2, $J_{2,3}$=2.5 Hz), 4.53 (ddd, 1H, H-4, $J_{4,5}$=9.5 Hz, $J_{H,P}$=9.5 Hz), 6.09 (ddd, 1H, CHF2, $J_{H,F}$=49.0 Hz, $J_{H,P}$=24.0 Hz).

General methods and materials

Myo-inositol was purchased from Pfanstiehl Laboratories Inc. (USA).

1-Hydroxy-6-trifluoromethylbenzothiazole (see W. König and R. Geiger, Chem. Ber. 103, 788, (1970)) and 1,2,4-triazole were dried in vacuo over P2O5 for 70 h at 50° C.

Triethylammonium bicarbonate buffer (TEAB, 2M): a mixture of triethylamine (825 ml) and H2O (2175 mL) was saturated with carbon dioxide gas at 0° C. until pH 7.0.

Column chromatography was performed on Merck Kieselgel 60 (230–400 mesh, ASTM). Melting points are uncorrected.

1H-NMR spectra were recorded on a Bruker WM-300 spectrometer, equipped with an ASPECT-2000 computer operating in the Fourier transform mode at 300 MHz. 31P-NMR spectra were recorded on a Jeol JNM-FX 200 spectrometer on line with a JEC 980B computer at 50.1 and 80.7 MHz, respectively. 1H-chemical shifts are given in ppm (delta) relative to tetramethylsilane (TMS) as internal standard and 31P-chemical shifts in ppm (delta) to 85% H3PO4 as external standard.

Synthesis of Bis(1-[6-trifluoromethyl]benzotriazolyl) methylphosphonate

A solution of methylphosphonic dichloride (0.67 g, 5.04 mmol) in anhydrous dioxane (5 ml) was added dropwise to a stirred solution of dry 1-hydroxy-6-trifluoromethylbenzotriazole (2.05 g, 10.10 mmol) and pyridine (0.81 ml, 10.03 mmol) in anhydrous dioxane (20 mL) at 20° C. The solution was stirred for 1 h at 20° C. and the salts were removed by filtration. The 0.2M stock solution of bis(1-[6-trifluoromethyl]benzotriazolyl) methylphosphonate (31P-NMR: delta 47.60) thus obtained could be stored for several weeks at −20° C.

Synthesis of (Difluoromethyl)phosphonic di(1,2,4-triazolide)

A solution of (difluoromethyl)phosphonic dichloride (see D. E. Bergstrom et al., J. Org. Chem. 53, 3953 (1988)) (0.85 g, 5.03 mmol) in anhydrous dioxane (5 ml) was added dropwise to a stirred solution of dry 1,2,4-triazole (0.85 g, 12.32 mmol) and Et3N (1.40 ml, 10.06 mmol) in anhydrous dioxane (20 ml) at 20° C. The solution was stirred for 1 h at 20° C. and the salts were removed by filtration. The 0.2 M stock solution of (difluoro-methyl)phosphonic di(1,2,4-triazolide) (31P-NMR: delta −3.01, $J_{P,F}$=106.0 Hz) thus obtained could be stored for several weeks at −20° C.

We claim:

1. A compound of the formula (I)

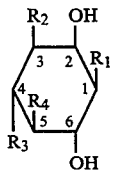

in which
$R^1$ is
1) phosphate
2) 1,2 diacyl-sn-glycer-3-yl phosphate, wherein acyl is a fatty acid with 2 to 20 C-atoms and 0 to 4 C—C-double bonds, or
3) 1,2 dialkyl-sn-glycer-3-yl phosphate, wherein alkyl is a hydrocarbon having 2 to 20 carbon atoms and 0 to 4 C—C double bonds $R^2$ is
1) OH, or
2) phosphate $R^3$ is
1) phosphate, or
2) OH
3) a radical of formula (II)

wherein
a) Y=Z=O and X=($C_1$-$C_8$)-alkyl
b) Y=Z=O and X=($C_1$-$C_{18}$)-aryl
c) Y=S and Z=O and X=($C_1$-$C_8$)-alkyl
d) Y=S and Z=O and X=($C_6$-$C_{18}$)-aryl
e) Y=O and Z=X=($C_1$-$C_8$)-alkyl
f) Y=O and Z=X=($C_6$-$C_8$)-aryl
g) Y=S and Z=X=($C_1$-$C_8$)-alkyl
h) Y=S and Z=X=($C_6$-$C_{18}$)-aryl
i) Y=Z=O and X=$CF_2$H
j) Y=O and Z=X=F
k) Y=Z=O and X=O—($C_1$-$C_8$)-alkyl
l) Y=Z=O and X=O—($C_6$-$C_{18}$)-aryl
m) Y=S and Z=O and X=O—($C_1$-$C_8$)-alkyl
n) Y=S and Z=O and X=O—($C_6$-$C_{18}$)-aryl
o) Y=O and Z=X=O—($C_1$-$C_8$)-alkyl
p) Y=O and Z=X=O—($C_6$-$C_{18}$)-aryl
q) Y=S and Z=X=O—($C_1$-$C_8$)-alkyl
r) Y=S and Z=X=O—($C_6$-$C_{18}$)-aryl
4) a radical of formula (III )

where
a) X=OR where R is H, ($C_1$-$C_8$) -alkyl, or ($C_6$-$C_{18}$) -aryl
b) X=($C_1$-$C_8$)-alkyl
c) X=($C_6$-$C_{18}$)-aryl
d) X=NH—($C_1$-$C_8$)-alkyl e) X=NH—(C6-C18)-aryl
5) a radical of formula (IV)

(IV)

where
a) X=OR where R is (C1-C8)-alkyl or (C6-C18)-aryl
b) X=(C1-C8)-alkyl
c) X=(C6-C18)-aryl
d) X=NH—(C1-C8)-alkyl
e) X=NH—(C6-C18)-aryl
wherein when $R^2$ is OH, $R^3$ is not OH
$R^4$ is
1) a radical of formula (V)

(V)

where
a) Y=Z=O and X=(C1-C8)-alkyl
b) Y=Z=O and X=(C1-C18)-aryl
c) Y=S and Z=O and X=(C1-C8)-alkyl
d) Y=S and Z=O and X=(C6-C18)-aryl
e) Y=O and Z=X=(C1-C8)-alkyl
f) Y=O and Z=X=(C6-C18)-aryl
g) Y=S and Z=X=(C1-C8)-alkyl
h) Y=S and Z=X=(C1-C18)-aryl
i) Y=Z=O and X=CF2H
j) Y=O and Z=X=F
k) Y=Z=O and X=O—(C1-C8)-alkyl
l) Y=Z=O and X=O—(C6-C18)-aryl
m) Y=S and Z=O and X=O—(C1-C8)-alkyl
n) Y=S and Z=O and X=O—(C6-C18)-aryl
o) Y=O and Z=X=O—(C1-C8)-alkyl
p) Y=O and Z=X=O—(C6-C18)-aryl
q) Y=S and Z=X=O—(C1-C8)-alkyl
r) Y=S and Z=X=O—(C6-C18)-aryl
2) a radical of formula (VI)

(VI)

wherein a) X=OR where R is H, (C1-C8)-alkyl, or (C6-C18)-aryl
b) X=(C1-C8)-alkyl
c) X=(C6-C18)-aryl
d) X=NH—(C1-C8)-alkyl
e) X=NH—(C6-C18)-aryl
3) a radical of formula (VII)

(VII)

wherein
a) X=OR where R is (C1-C8)-alkyl or (C6-C18)-aryl
b) X=(C1-C8)-alkyl
c) X=(C6-C18)-aryl
d) X=NH—(C1-C8)-alkyl
e) X=NH—(C6-C18)-aryl
and the physiologically tolerated salts thereof.

2. A compound of the formula (I) as claimed in claim 1, in which
$R^1$ is phosphate or 1,2-diacyl-cn-glycer-3-yl-phosphate, wherein acyl is a fatty acid radical having 2 to 20 carbon atoms and 0 to 4 C—C-double bonds,
$R^2$ is OH or phosphate,
$R^3$ is phosphate,
$R^4$ is a radical of formula (V)

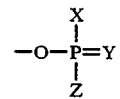
(V)

wherein Y=Z=O and X=(C1-C8)-alkyl, and the physiologically tolerated salts thereof.

3. A compound of formula (I) as claimed in claim 2, in which R4 is a radical of the formula (V) wherein X is methyl, ethyl or propyl.

4. A pharmaceutical composition comprising an effective amount of a compound as claimed in claim 1, or a physiologically tolerated salt therof, and a physiologically acceptable vehicle.

5. A method of treating a patient in need of a calcium-antagonist comprising,
administering an effective amount of the compound of formula (I) as claimed in claim 1.

6. A method of claim 5 for treating cardiovascular disease.

* * * * *